(12) United States Patent
Stoltz et al.

(10) Patent No.: US 7,112,309 B2
(45) Date of Patent: Sep. 26, 2006

(54) METHOD AND APPARATUS FOR USE OF REACTED HYDROGEN PEROXIDE COMPOUNDS IN INDUSTRIAL PROCESS WATERS

(75) Inventors: Michael J. Stoltz, Duncansville, PA (US); Stephen R. Temple, Santa Cruz, CA (US)

(73) Assignee: Steen Research LLC, West Linn, OR (US)

( * ) Notice: Subject to any disclaimer, the term of this patent is extended or adjusted under 35 U.S.C. 154(b) by 0 days.

(21) Appl. No.: 10/704,238

(22) Filed: Nov. 7, 2003

(65) Prior Publication Data

US 2004/0115112 A1 Jun. 17, 2004

Related U.S. Application Data

(62) Division of application No. 09/797,859, filed on Mar. 2, 2001, now Pat. No. 6,645,450.

(60) Provisional application No. 60/186,694, filed on Mar. 3, 2000.

(51) Int. Cl.
*B01D 53/78* (2006.01)
*B01D 53/18* (2006.01)
*B01D 53/14* (2006.01)
*B01D 53/38* (2006.01)
*B01D 53/86* (2006.01)

(52) U.S. Cl. .................. 422/171; 422/111; 422/172

(58) Field of Classification Search ............... 422/177, 422/180, 110, 111, 171, 172, 168, 4, 5, 122, 422/123
See application file for complete search history.

(56) References Cited

U.S. PATENT DOCUMENTS

| 3,021,189 | A | * | 2/1962 | Mancke et al. ............. 423/220 |
| 3,717,701 | A | | 2/1973 | Carlson |
| 3,905,774 | A | * | 9/1975 | Kotting ...................... 422/172 |
| 3,989,465 | A | * | 11/1976 | Onnen ......................... 422/110 |
| 4,002,722 | A | | 1/1977 | Suzuki et al. |
| 4,172,880 | A | * | 10/1979 | Tzavos ................... 423/245.2 |
| 4,203,765 | A | | 5/1980 | Claeys et al. |
| 4,443,342 | A | | 4/1984 | Stas et al. |
| 4,595,577 | A | | 6/1986 | Stas et al. |
| 4,614,646 | A | | 9/1986 | Christiansen |
| 5,019,339 | A | * | 5/1991 | Keeney et al. ................. 422/3 |
| 5,567,402 | A | * | 10/1996 | Vicard et al. ............ 423/245.2 |
| 5,945,078 | A | | 8/1999 | Taylor et al. |
| 6,015,536 | A | | 1/2000 | Lokkesmoe et al. |
| 6,645,450 | B1 | | 11/2003 | Stoltz et al. |

FOREIGN PATENT DOCUMENTS

| DE | 19753117 A1 | 6/1998 |
| DE | 19824903 C1 | 2/2000 |

(Continued)

OTHER PUBLICATIONS

International Search Report, date mailed Oct. 24, 2001, for PCT/US01/06875.

(Continued)

*Primary Examiner*—Stanley S. Silverman
*Assistant Examiner*—Ardith E Hertzog
(74) *Attorney, Agent, or Firm*—Morgan, Lewis & Bockius, LLP.

(57) ABSTRACT

Methods and apparatus are described which utilize an aqueous hydrogen peroxide composition of hydrogen peroxide and at least one additive which serves to catalyze the rapid decomposition of the hydrogen peroxide into hydroxyl radicals. When contacted with an atmospheric effluent containing odor and/or noxious components, the hydroxyl radicals formed oxidize the odor and noxious components to non-odor offensive, environmentally acceptable by-product.

26 Claims, 2 Drawing Sheets

FOREIGN PATENT DOCUMENTS

| JP | 01317528 | 12/1989 |
| JP | 09094431 | 4/1997 |

OTHER PUBLICATIONS

Rempp et al., "Polymer Synthesis", 2d rev. Edition (1991), Hüthig & Wepf Verlag Basel, New York, p. 56.

"Use of Hydrogen Peroxide in Gas Scrubbing", Effluent and Water Treat, J. vol. 19, pp. 20-22, Aug. 1979.

"Storage and Handling of Hydrogen Peroxide", Effluent and Water Treat, J. vol. 19, pp. 34-37, Aug. 1979.

"Analysis of Aqueous Effluents", Effluent and Water Treat. J. vol. 19, pp. 29-33 Aug. 1979.

"Advantages of Peroxygen Products in Pollution Control", Effluent and Water Treat. J. vol. 19, pp. 4-5, Aug. 1979.

"Fenton's Reagent Iron Catalyzed Hydrogen Peroxide" www.h2o2.com/applications/industrialwastewater/fenton-sreagent.html.

"Catalytic Oxidation of Phenol With Hydrogen Peroxide," report from *Interox Chemicals Ltd.*, Aug. 12, 1978.

Yunfu Sun and Joseph J. Pignatello, 1992, "Chemical Treatment of Pesticide Wastes. Evaluation of FE(III) Chelates for Catalytic Hydrogen Peroxide Oxidation of 2,4-D at Circumneutral pH," *J. Agric. Food Chem* 1992, 40. 322-327.

Written Opinion, (Feb. 25, 2002), International Preliminary Examining Authority, European Patent Office, PCT/US01/06875 (STENP004WO).

\* cited by examiner

METHOD AND APPARATUS FOR USE OF REACTED HYDROGEN PEROXIDE COMPOUNDS IN INDUSTRIAL PROCESS WATERS

CROSS-REFERENCES TO RELATED APPLICATIONS

This patent application is a divisional application of U.S. patent application Ser. No. 09/797,859, filed on Mar. 2, 2001, now U.S. Pat. No. 6,645,450, which claims the benefit of U.S. Provisional Application No. 60/186,694, filed Mar. 3, 2000. Both of these applications are incorporated by reference herein in their entirety.

FIELD OF THE INVENTION

This invention relates to the use of hydrogen peroxide reacted with strong reducing agents or stronger oxidizing agents to produce hydroxyl radicals. More specifically, the invention relates to utilizing in situ generation of the hydroxyl radical to effectively oxidize odor and/or noxious compounds found in the food processing industry, such as poultry, beef or fish processing, as well as rendering of meat, fish or fowl by-products. This invention also relates to the use of the hydroxyl radical in the reduction of volatile organic compounds in aqueous gas scrubbers.

BACKGROUND OF THE INVENTION

In the processing of poultry, beef, and fish, the large volume of organic material processed, as well as secondary processing (rendering), can generate large quantities of odiferous gases including organic sulfides, thiols, amines, alcohols, inorganic sulfides, ammonia, and simple carboxylic acids. These compounds are usually the result of biological action on the organic materials being processed. The odors produced are offensive and can travel significant distances to surrounding real estate. In other industries, such as chemical processing, paint production, wastewater treatment, etc., noxious compounds, such as volatile organic compounds (VOCs), are produced and are subject to environmental air quality regulations.

These gases are usually captured by a water media in air scrubber systems. In an air scrubber system, typically, air from the processing step is evacuated into a tower where water, broken into droplets either by contact with mixed media or distribution channels, absorbs the odiferous and noxious gas compounds. This water is recirculated and discharged typically to wastewater treatment systems. U.S. Pat. No. 6,015,536 to Lokkesmoe et al., provides a detailed description of the available air scrubbing systems on the market and is hereby incorporated by reference.

It can readily be seen that the scrubbing water media will quickly saturate with the offensive gases and lose its absorbing potential. At this point, the water has an intense disagreeable odor. Additives are commonly injected into the scrubbing water stream to reduce the odor content of the aqueous scrubbing media. The water is either dumped to the wastewater treatment facility or a portion is withdrawn to the wastewater facility while fresh makeup water is added to account for the difference.

It can also be seen that as the water saturates with gases, particularly nitrogen (ammonia) bearing gases, the pH of the water will rise proportionally. This marked increase in pH reduces the solubility of the gases causing them to flash to the atmosphere. This results in a decrease in the efficiency of the gas transfer to the water media.

Numerous attempts have been made to reduce the odor components in the air scrubbing system. Some technologies attempt to reduce the odor by injecting a maskant, which is a stronger, more pleasing odor compound. These maskants are extremely expensive, and the duration of the effectiveness is very short. These compounds do nothing to the actual structure of the odor molecule.

Maskants are also "fogged" or injected into spray orifices under high pressure to create a small droplet mist effect. These misted materials are directed into the atmosphere around the odor causing process. The misted materials either mask the odor or combine with the odor-causing molecule in the atmosphere to temporarily lower the offensive odor. These compounds, which are usually essential oils, are then blown with the prevailing winds. These materials are limited by extreme cost, and do nothing to actually affect the odor-causing molecule.

U.S. Pat. Nos. 4,443,342 and 4,595,577, to Stas et al., describe a treatment method using hydrogen peroxide and copper sulfate as the catalyst for treatment of wastewater and gases containing organic sulphur compounds in a pH range below 6.5. It is well known to those of skill in the art that the efficiency of hydrogen peroxide as an oxidizer is increased in the pH range of 3 to 6.5. Stas et al. also describe using hydrogen peroxide in acidic aqueous media with 1 to 5 ppm of ferric sulfate as a catalyst when comparing the efficacy of the use of copper. This catalyst choice, in the amount used, only increases the efficiency of the hydrogen peroxide and does not effectively reduce the hydrogen peroxide to free radicals in the quantities that would be needed to oxidize odor components to soluble compounds to enable their removal.

Hydrogen peroxide by itself has only moderate success in air scrubbing systems. It reacts very slowly and is limited in the number of organic molecules it can oxidize. Some odor reduction can be achieved using hydrogen peroxide, but it is usually via microbiological control or increase of oxygen content of the aqueous scrubbing media.

Halogen donors such as chlorine dioxide, chlorine gas, sodium hypochlorite, and hypobromous acids have had limited success in the art. The low electronegativity of these halogens (1.0 to 1.7 volts) limit their ability to oxidize odor constituents down to simple soluble compounds. Therefore their odor removal efficiency is low compared to the quantity needed. The use of halogen donors is falling under environmental scrutiny due to the formation of haloamines as well as trihalomethanes. Use of these halogens in aqueous streams eventually contributes to trihalomethanes and haloamines in surface waters.

U.S. Pat. No. 6,015,536, to Lokkesmoe et al, describes the use of peroxyacid compounds at a pH of 3 to 6 for odor reduction in air scrubbers. Peroxy acid, namely peracetic acid, is used as an oxidizer of odor causing molecules, and a reduction of odors from 5 to 50% is described. However, the large doses of peracetic acid needed, preclude higher odor removal rates due to cost as well as the contribution of a pungent odor from the acetic and peracetic acids. The peracid compounds also lack sufficient electronegative potential to break up odor causing compounds to the degree needed for greater than 50% removal rates.

Ozone has been used with limited success in aqueous gas scrubbers. Ozone has an inherent high capital expenditure cost and is difficult to utilize the ozone gas in aqueous media. It is difficult to force enough gas into contact with the aqueous media to effectively oxidize odor compounds into simple soluble reduced-odor compounds. Ozone is also characterized by large electric utility costs associated with corona discharge type ozone production units.

Inorganic percompounds, such as percarbonates, persulfates, perborates, and permangenates, have demonstrated odor control potential. These compounds, however, are notoriously slow to liberate oxygen in cold water at elevated pH.

There exists a need in the art for a treatment process that has a high enough electronegative potential to reduce substantially all odor and/or noxious compounds to simple, soluble, reduced-odor/noxious or odor/noxious-free compounds. This treatment process would offer even greater advance in the art if the process could also eliminate or greatly reduce the high cost of treating the scrubber water effluent in the wastewater treatment process.

SUMMARY OF THE INVENTION

Broadly speaking, the present invention relates to chemical compositions, systems and processes for removing odor and noxious components from an atmospheric effluent using an aqueous hydrogen peroxide composition of hydrogen peroxide and an additive that catalyzes the decomposition of hydrogen peroxide into hydroxyl radicals. Preferably, the catalyst is used in a manner that decomposes hydrogen peroxide to predominantly hydroxyl radicals (in distinction from predominantly molecular oxygen). When contacted with the atmospheric effluent, the aqueous hydrogen peroxide composition oxidizes the odor and noxious components to non-odor offensive, environmentally acceptable by-product. Several embodiments of the invention are discussed below.

As a method for removing at least one of an odor component and a noxious component from an atmospheric effluent, in one embodiment of the present invention, the atmospheric effluent is contacted with an aqueous hydrogen peroxide composition including hydrogen peroxide and at least one additive that catalyzes the decomposition of the hydrogen peroxide to predominantly produce hydroxyl free radicals; the odor component and/or noxious component in the atmospheric effluent is oxidized substantially to non-odor-offensive, environmentally acceptable by-product; the oxidation produces a liquid effluent containing the by-product and the aqueous hydrogen peroxide composition, and an exhaust effluent having reduced amounts of the odor component and/or noxious component. In further embodiments, the hydrogen peroxide composition may further include wetting agents and chelating agents.

As a packed scrubber system for removing at least one of an odor component and a noxious component from an atmospheric effluent, in another embodiment of the present invention, the system includes: a packed scrubber tank which includes an atmospheric effluent inlet for introducing the atmospheric effluent into the packed scrubber tank; a packed column for providing an increased surface area on which the atmospheric effluent can contact an aqueous hydrogen peroxide composition that can oxidize the odor component and/or noxious component to produce substantially non-odor-offensive, environmentally acceptable by-product which exits the packed column with the aqueous hydrogen peroxide composition as a liquid effluent, and a gaseous exhaust effluent having reduced amounts of the odor component and/or noxious component; at least one dispenser arranged for delivering the aqueous hydrogen peroxide composition into the packed column; a reservoir for collecting the liquid effluent; an atmospheric vent for outletting the exhaust effluent from the scrubber tank; and an aqueous hydrogen peroxide composition delivery system connected to the packed wet scrubber tank including: at least one sidestream effluent pump for delivering an aqueous hydrogen peroxide composition to the dispenser(s) and in fluid communication to the reservoir to withdraw a portion of the liquid effluent as a sidestream effluent on the vacuum-side of the sidestream effluent pump and connected to the dispenser(s) on the backstream side of the sidestream effluent pump, wherein the aqueous hydrogen peroxide composition including hydrogen peroxide and at least one additive that decomposes the hydrogen peroxide predominantly to hydroxyl free radicals, the aqueous hydrogen peroxide composition being added to the sidestream effluent for delivery to the dispenser(s).

As a system for scrubbing gaseous effluent, in another embodiment of the present invention, the system includes: a packed column which includes a gaseous effluent inlet, a packing region for housing packing for contacting the gaseous effluent with an aqueous hydrogen peroxide composition, and a gaseous effluent outlet that directs the gaseous effluent out of the packed column after it has contacted the aqueous hydrogen peroxide composition in the packing region; a sidestream subsystem including at least one pump and plumbing arranged with respect to the packed column to remove the aqueous hydrogen peroxide composition from the packed column after it has contacted the gaseous effluent and introduce the aqueous hydrogen peroxide composition into the packing region; a source of hydrogen peroxide arranged to provide the hydrogen peroxide to the sidestream subsystem; and, a source of at least one additive arranged to provide the additive to the sidestream subsystem so that the additive mixes with the hydrogen peroxide in the sidestream subsystem to decompose the hydrogen peroxide to hydroxyl free radicals and thereby produce the aqueous hydrogen peroxide composition.

Other advantages of the present invention will become apparent from the following detailed description taken in conjunction with the accompanying drawings that illustrate, by way of example, the principles of the invention.

BRIEF DESCRIPTION OF THE DRAWINGS

The present invention will be better understood by reference to the following description taken in conjunction with the accompanying drawings in which.

DETAILED DESCRIPTION OF THE INVENTION

Figure 1:
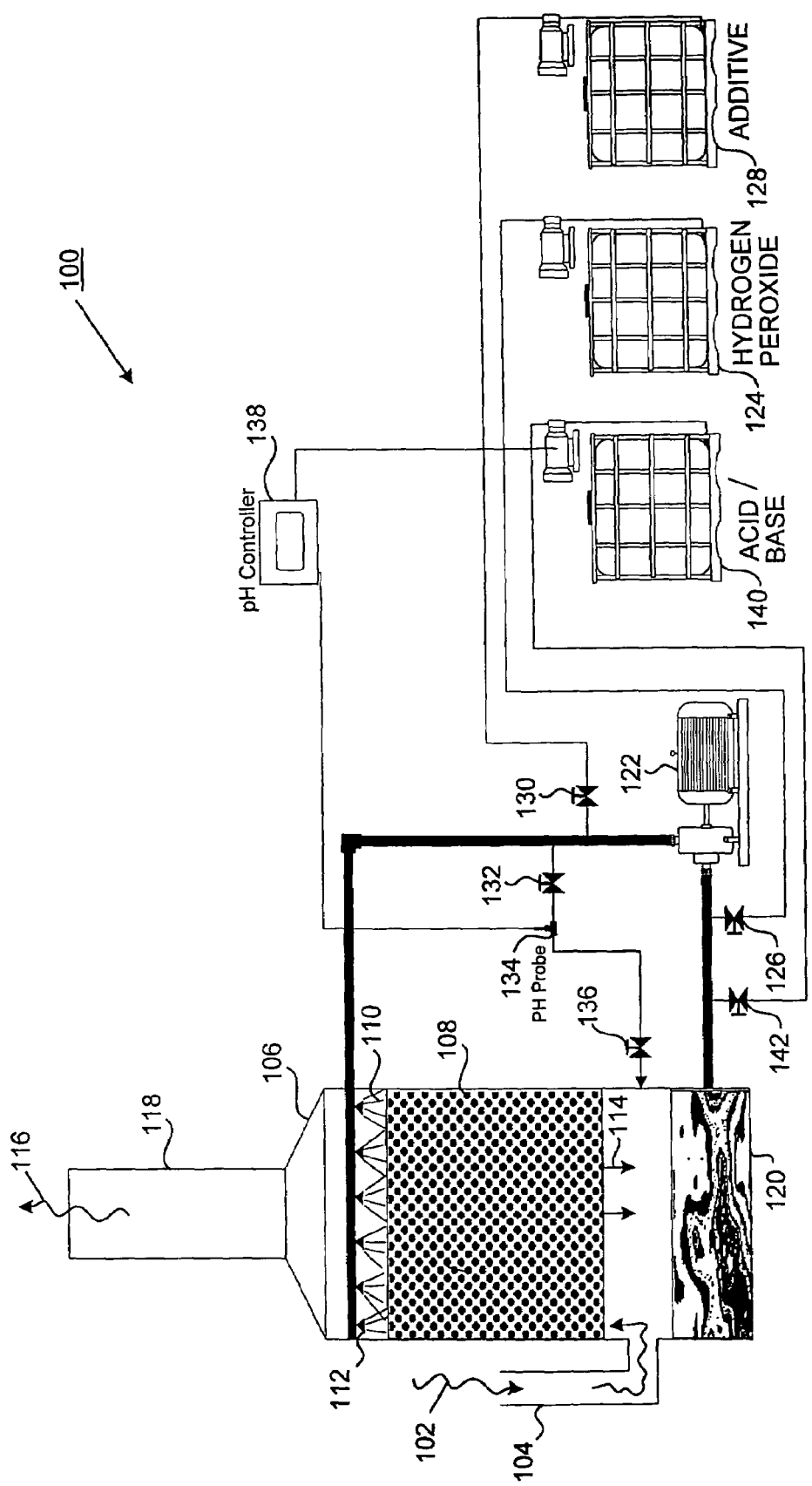
FIG. 1 shows a diagram of a wet scrubber system in which the process for removing an odor and/or noxious component from an atmospheric effluent using an aqueous hydrogen peroxide composition may be practiced according to one embodiment of the present invention.

The present invention will now be more fully described with reference to the accompanying drawings. To facilitate explanation, the invention will be described primarily in the context of a particular embodiment of a wet scrubber tower. While the invention will be described in conjunction with this particular embodiment, it should be understood that the invention can be applied to a wide variety of applications and it is intended to cover alternatives, modifications, and equivalents as may be included within the spirit and scope of the invention as defined by the appended claims.

The present invention uses an aqueous hydrogen peroxide composition of hydrogen peroxide and at least one additive, which serves to catalyze the rapid decomposition of the hydrogen peroxide into hydroxyl radicals. When contacted with an atmospheric effluent containing odor and/or noxious components, the hydroxyl radicals formed oxidize the odor and noxious components to non-odor offensive, environmentally acceptable by-product. The by-product in combination with the aqueous hydrogen peroxide composition form a liquid effluent which provides charge neutralizing and adsorption species which aid in treatment of wastewater effluents.

As can be seen in Table 1 below, the hydroxyl radical is known in the art as the second most electronegative species, second only to fluorine, and is significantly higher in oxidation potential than other compounds known in the art. It is not the intent of the invention to utilize the oxidation potential of the hydrogen peroxide, but rather the hydroxyl radical produced from the decomposition of the hydrogen peroxide. It will be appreciated that in the decomposition of hydrogen peroxide some diatomic oxygen may also be produced also having an oxidation potential, however, the present invention is directed at driving the decomposition reaction to produce predominantly hydroxyl radicals to act in the oxidation of the odor and/or noxious components in the atmospheric effluent.

TABLE 1

| Oxidizer | Oxidation Potential (Volts) |
|---|---|
| fluorine | 3.0 |
| hydroxyl radical | 2.8 |
| ozone | 2.1 |
| hydrogen peroxide | 1.8 |
| potassium permanganate | 1.7 |
| hypobromous acid | 1.6 |
| chlorine dioxide | 1.5 |
| chlorine | 1.4 |

This use the present invention offers many advantages. First, the highly electronegative hydroxyl radical is capable of a much greater decomposition of odor-causing molecules than any composition known in the art. Further, the use of some of the decomposition additives, particularly, ferrous sulfate, not only reduces the hydrogen peroxide into the hydroxyl radicals, but also introduces a semi-colloidal substrate into the aqueous media that is capable of effective adsorption of odor-causing compounds. Additionally, when the gas/water scrubber water, e.g., the liquid effluent, is evacuated to a wastewater treatment facility, for example, by dumping the entire liquid content of the scrubber or by continuous overflow of the scrubber system, the wastewater treatment influent is "pretreated" by cationic ferric hydroxide complexes in the liquid effluent which offer effective colloidal charge neutralization as well as adsorption of wastewater constituents into its floc matrix. The addition of a charge neutralizing/adsorption species is always an added cost at the wastewater treatment plant. By use of the present invention, that cost is eliminated or greatly reduced.

FIG. 1 shows a diagram of a wet scrubber system 100 in which the process for removing an odor and/or noxious component from an atmospheric effluent using an aqueous hydrogen peroxide composition may be practiced according to one embodiment of the present invention. According to the present embodiment, an atmospheric effluent 102 enters a packed scrubber tank 106 through an atmospheric effluent intake 104. The atmospheric effluent 102 may be from a food processing process, rendering process, or other industrial process which produces an atmospheric effluent having odoriferous and/or noxious components. The atmospheric effluent 102 enters a packed column 108 where it is contacted with an aqueous hydrogen peroxide composition 110 includes hydrogen peroxide and at least one additive that catalyzes the decomposition of the hydrogen peroxide to predominantly hydroxyl radicals. Thus, the hydrogen peroxide composition leaving dispenser(s) 112 has an unusually high concentration of hydroxyl radicals.

In the packed column 108, the hydroxyl radicals oxidize the odor and/or noxious components in the atmospheric effluent 102 producing substantially non-odor-offensive, environmentally-acceptable by-product which exit the packed column 108 with the aqueous hydrogen peroxide composition as a liquid effluent 114, and producing a gaseous exhaust effluent 116 having reduced amounts of the odor and/or noxious components. The exhaust effluent 116 exits the scrubber tank by way of a vent 118.

Dependent on the oxidation of the odor and/or noxious component, the liquid effluent 114 may contain by-product that is soluble in the aqueous hydrogen peroxide composition or may adsorb onto semi-colloidal particles formed in the aqueous hydrogen peroxide composition. The liquid effluent 114 exits the packed column 108 and is collected in a reservoir 120.

The reservoir 120 collects the liquid effluent 114 from the oxidation process for discharge to a wastewater facility. In some embodiments, the liquid effluent 114 may be collected and the entire reservoir 120 dumped into a waste treatment pathway or waste treatment facility. In other embodiments, the reservoir 120 may be equipped with an overflow system so that a portion of the liquid effluent 114 is continually overflowed into a waste treatment pathway for delivery to a waste treatment facility. In the latter case, the reservoir 120 may also have an add-back line to allow introduction of makeup water into the reservoir 120 so that a constant effluent level is maintained in the reservoir 120. The reservoir 120 may also be vented.

A pump 122 in fluid communication with the reservoir 120 withdraws a sidestream of the liquid effluent 114 toward the vacuum side of the pump 122. Those of skill in the art will appreciate that a wide variety of pumps may be used. The pump should be chosen to provide sufficient power to move fluid at the mass flow rate required by the particular scrubber. It should also resist chemical attach by the liquid effluent and any additives provided thereto. For certain applications, specific types of pumps will be required. For example, as described below, when the pump is used to introduce ozone or other gaseous catalyst, a regenerative turbine pump is preferred.

It will be appreciated that at the start of a process the contents of the reservoir 120 may be essentially makeup water until the process has completed several cycles in which the aqueous hydrogen peroxide composition 110 has been contacted with the atmospheric effluent 102. In one embodiment, the sidestream effluent is used to deliver the aqueous hydrogen peroxide composition to the atmospheric effluent 102 in the packed column 108. The hydrogen peroxide of the aqueous hydrogen peroxide composition is delivered from a source container 124 into the sidestream effluent via an inlet valve 126. In one example, the hydrogen peroxide source may be 50% by weight hydrogen peroxide solution.

The hydrogen peroxide enriched sidestream effluent is then pumped to the backstream side of the pump 122 where at least one decomposition additive is delivered from a source container 128 into the hydrogen peroxide enriched sidestream effluent via an inlet valve 130. In one example, the additive may be a 38% solution of ferrous sulfate. Upon the addition of the additive on the backstream side of the pump 122, the hydrogen peroxide is decomposed to hydroxyl radicals (predominantly hydroxyl radicals in one embodiment) forming the aqueous hydrogen peroxide composition 110. Addition of the additive on the backstream side of the pump 122 is preferred over arrangements on the vacuum side as it reduces wear on the pump 122 from the decomposition product of hydrogen peroxide, e.g., the hydroxyl radicals. The aqueous hydrogen peroxide composition is then delivered to the packing column 108 via dispensers 112 to contact the atmospheric effluent 102.

In other embodiments, the aqueous hydrogen peroxide composition may further include additional additives, wetting agents, and/or chelating agents, further discussed herein. Addition of these compounds would be made similar to the addition of the additive discussed in regard to FIG. 1. Thus, there may be separate source containers and inlet valves to enable the regulated delivery of these compounds to the sidestream effluent. Preferably, the addition would occur on the backstream side of the pump 122, however other arrangements may be used. Additionally, some or all of the other additives, wetting agents and/or chelating agents may be mixed together, and delivered from a single source container. Alternatively, any one or more of these additives may be provided together with one or more other source materials. For example, the hydrogen peroxide in source 124 may contain any one or more chemically compatible additives such as certain chelating agents and/or wetting agents. Of course, the additives may also be provided with the decomposition additive from source 128 and/or the acid or base from a source 140.

It will be appreciated that the inlet valves discussed in FIG. 1 are regulated so that the aqueous hydrogen peroxide composition in the sidestream has a desired composition. Regulation of the inlet valves may be by any means, such as a controller, or formulator system, such that the individual components are delivered into the sidestream effluent in the desired amounts to form the aqueous hydrogen peroxide composition. Further, this system may stand-alone or be incorporated as part of a larger control system. It will be appreciated that other embodiments may be utilized in which the components of the aqueous hydrogen peroxide composition are added at different locations within the system.

The system and process of the present invention may also include a pH control loop, which can measure the pH of the sidestream effluent and then regulate the addition of an acid or base into the sidestream effluent to maintain the pH within a preferred pH range. In this embodiment, an inlet valve 132 permits the withdrawal of a portion of the effluent sidestream downstream from the inlet valve 130 to a pH probe 134. The sidestream effluent contacts the pH probe 134 and passes back out into the scrubber tank 106 through inlet valve 136 for collection in the reservoir 120. The pH probe 134 measures the pH of the sidestream effluent and communicates the information to a pH controller 138. The pH controller 138 then regulates, as needed, the addition of an acid or base from an acid or base source container 140 into the sidestream effluent via an inlet valve 142. In the present embodiment, the inlet valve 142 is located upstream from the inlet valve 126. Through the addition of the pH control loop, the pH of the sidestream effluent is maintained at a level that maximizes the decomposition of the hydrogen peroxide by the additives.

In the present invention, several additives, alone or in combination, may be used with the hydrogen peroxide to form the aqueous hydrogen peroxide composition, their choice depending on cost, environmental concern and organic loading of the effluent being treated.

In one embodiment, the additive used with the hydrogen peroxide in forming the aqueous hydrogen peroxide composition is ferrous sulfate. The use of ferrous sulfate in sufficient quantities to decompose the hydrogen peroxide into hydroxyl radicals is well known to those of skill in the art as "Fenton's reagent". The use of Fenton's reagent in odor reduction of mercaptans and sulfides has been explored in the oil and pulp and paper industries. The use of Fenton's reagent has also been explored for color removal in aqueous media as well as in the batch reaction breakdown of ring-structured organics, i.e., cresols, phenolic compounds. The use of the highly electronegative hydroxyl radical has not been explored in air scrubbers, such as those utilized in food processing, and in other process industries which produce atmospheric effluents containing odor and/or noxious components, for example, volatile organic compounds (VOCs).

In aqueous media, ferrous iron decomposes hydrogen peroxide in the following manner:

$$Fe^{2+} + H_2O_2 \longrightarrow Fe^{3+} + OH^- + OH^*$$

As earlier described, the hydroxyl radical formed oxidizes the odor producing components and/or noxious components via electron transfer.

In one embodiment of the present invention, the aqueous hydrogen peroxide composition is formed using a 50% by weight hydrogen peroxide solution and a 38% ferrous sulfate solution. The concentration of hydrogen peroxide in the source should be chosen to allow safe handling given the equipment in use and to provide sufficient concentration for the needs of the scrubber. Although the concentration of hydrogen peroxide in the source may be selected within a wide range, specific embodiments will range between about 35% to 50% by weight in an aqueous solution as these ranges are currently industrially available and legally transportable. In a preferred embodiment, the concentration is about 50% by weight in aqueous solution.

The catalyst source is also chosen with a view toward safety and effectiveness. Obviously, the concentration will vary depending upon the catalyst chosen for the task. Typically, an aqueous solution will be employed, although for ozone and certain of the group VII elements, a direct gaseous addition will be necessary. The solubility limit of the catalyst presents an upper bound on concentration of the source catalyst. In the case of ferrous sulfate, the concentration may be selected within a wide range with specific embodiments within the range between about 20% to about 38% by weight in aqueous solution. In a preferred embodiment the concentration of ferrous sulfate is about 38% by weight in aqueous solution. The ratio by weight of the hydrogen peroxide solution to the ferrous sulfate, based on a 50% by weight hydrogen peroxide solution and a 38% by weight ferrous sulfate solution should be within the range between about 1:1 to about 100:1, with a preferred ratio within the range between about 2:1 to about 50:1, and with a most preferred ratio within the range between about 5:1 to about 15:1. The higher the ferrous sulfate ratio the more the decomposition reaction is driven to radical production. The ratio can be as high as one part 50% by weight hydrogen peroxide solution to ten parts 38% ferrous sulfate solution, but an extreme amount of heat is generated. While this amount of heat may be acceptable in some settings, it may not be desirable in others.

In other embodiments, additives, other than ferrous sulfate, or in combination with ferrous sulfate, may be used. In one embodiment, the additive may be any element chosen from elements in groups 3B, 4B, 5B, 6B, 7B, 8B, 1B and 2B of the Periodic Table of Elements, and combinations thereof. More preferred are the "d" block transition elements, characterized by the "d" electrons in their valence shell, and combinations thereof. For example, the additive may be cobalt. In one embodiment, the aqueous hydrogen peroxide composition may be formed using an amount of cobalt within the range between about 0.5% wt/wt % to about 1% wt/wt % of the total aqueous hydrogen peroxide composition. Or, the amount of cobalt may be between about 0.5% wt/wt % to about 1% wt/wt % of a solution comprised of cobalt and a 50% by weight hydrogen peroxide solution. In another embodiment, the additive may be any element selected from elements in group 7A of the Periodic Table of Elements, and combinations thereof, for example, fluorine.

In another embodiment, the additive may be ozone. When using ozone as the hydrogen peroxide decomposition agent, very poor gas transfer to liquid media has been observed in the art. As part of the present invention, use of a regenerative turbine pump, for example, a Burks regenerative turbine pump manufactured by Burks Manufacturing is used as the pump 122. Referring to FIG. 1, use of a regenerative turbine pump as pump 122 operating with the hydrogen peroxide enriched aqueous sidestream effluent on the vacuum side with the ozone/air mixture in the inlet port pre-built on the vacuum side and pressurized on the discharge side to a minimum of 100 psi by a pinch valve, gives an excellent gas transfer to liquid media. In this instance, rather than the ozone being delivered through inlet valve 130, it would instead be connected to the inlet port pre-built on the vacuum side of the regenerative turbine pump 122 and regulated through the pinch valve. It will be appreciated that this pinch valve may also be controlled using the same control system or formulator system that regulates the other inlet valves of FIG. 1.

As the hydrogen peroxide enriched sidestream effluent enters the vacuum side of the regenerative turbine pump, the air/ozone mixture is also introduced through a pre-machined air port. The intense shear developed, breaks the ozone/air mixture into microbubbles entrained in the hydrogen peroxide enriched effluent. The discharge of the pump is pressurized to a minimum of 100 psi through a pinch valve assembly, ensuring solubilization of the ozone into the hydrogen peroxide enriched effluent. This allows for the efficient decomposition of the hydrogen peroxide by the ozone into hydroxyl radicals.

It will be readily apparent to one of normal skill in the art that the additive(s) selected from these elements would be chosen based upon cost, speed of reaction and environmental impact. Among these elements, iron and its conjugates are the cheapest, most readily available, and are of lowest environmental impact.

In a further embodiment of the present invention, a nonionic wetting agent may be added to the aqueous hydrogen peroxide composition to enhance activity by allowing further penetration of the oxidizing agent into crevices of bacterial forms of odor and/or noxious components. While the exact mechanism is not known, it is believed that certain nonionic surfactants, i.e., wetting agents, assist in the degradation of bacterial cell walls allowing the aqueous hydrogen peroxide composition to more readily kill the bacteria in the medium.

Preferred wetting agents are octylphenols, ethylene oxide block copolymers and propylene oxide block copolymers, and combinations thereof. The determining factors for wetting agent choice is organic loading of the effluent, i.e., the level of proteins or starches in the effluent, cleanliness of the system being treated, i.e., the amount of deposits and slime on the surfaces of the scrubber tank and packing, as well as need for defoaming capabilities.

In one embodiment, the wetting agent, as 100% active material, is present in an amount within the range up to about 10% by weight of the aqueous hydrogen peroxide composition (in the scrubber or as additives to a scrubber sidestream), with a preferred embodiment within the range up to about 5% by weight of the aqueous hydrogen peroxide composition, and in a most preferred embodiment within the range up to about 1% by weight of the aqueous hydrogen peroxide composition.

In a further embodiment of the present invention, a low molecular weight dispersant polymer may be added to the composition in order to prevent iron and other particle agglomeration in the aqueous media being treated as well as prevention of iron and organic deposition in lower flow areas. In one embodiment, the weight average molecular weight of these low molecular weight dispersants is within the range between about 1,000 to about 22,000, with a preferred weight average molecular weight within the range between about 1,000 to about 9,000. These low molecular weight dispersants may be, but are not limited to, homopolymers of acrylic acid, methacrylic acid, acrylamide, copolymers and terpolymers acrylates, methacrylates, acrylamide, AMPS (2-acrylamido-2-methyl propane sulfonic acid), and combinations thereof.

The low molecular weight dispersant polymer is added wt/wt % on the total composition weight of the aqueous hydrogen peroxide composition (in the scrubber or as additives to a scrubber sidestream). A preferred percentage of the low molecular weight dispersant, in the aqueous hydrogen peroxide composition is within the range between about 0.5% active wt/wt % to about 10% active wt/wt % of the total aqueous hydrogen peroxide composition. A more preferred percentage is within the range between about 0.5% active wt/wt % to about 5% active wt/wt % of the total aqueous hydrogen peroxide composition, and a most preferred percentage is within the range between about 0.5% active wt/wt % to about 2% active wt/wt % of the total aqueous hydrogen peroxide composition.

In a further embodiment of the present invention, the aqueous hydrogen peroxide composition may further include a chelating agent. As earlier discussed, a semi-collodial metal complex may form during the oxidation process, and in some instances, the development of this colloidal metal complex is undesirable. The chelating agent is added to prevent the formation of metal hydroxides or other insoluble metal complexes. In one embodiment, the chelating agents may be organic acids such as gluconic acids, glycolic acids, lactic acids, and combinations thereof. It will be appreciated that a large number of chelating agents may also be used and their selection readily apparent to those of skill in the art, however, the chelating agent should not be of such potent chelating ability as to prevent availability of the metal complex for decomposition purposes.

EXAMPLES

The following examples describe specific aspects of the present invention to illustrate the invention and aid those of skill in the art in understanding and practicing the invention. The examples should not be construed as limiting the present invention in any manner.

Example #1

Chicken feather processing scrubber water
Sample size 1,000 ml
pH=5.5 adjusted with sulfuric acid in the scrubber sump
Intense odor after treatment with chlorine dioxide
300 ppm 50% hydrogen peroxide added concurrent with 100 ppm ferrous sulfate solution (38%)
Reaction was instantaneous, solution removed to another air filtered room.
No detectable odor, slight chlorine smell detected.

Example #2

Rendering cooker
Sample Size 1,000 ml
pH adjusted to 5.5 with sulfuric acid
Very intense odor
300 ppm 50% hydrogen peroxide added concurrent with 100 ppm ferrous sulfate solution (38%)
Reaction was instantaneous, odors completely eliminated within 15 seconds.
Sample was allowed to set undisturbed for 48 hours. Odors did not reoccur.
In Example, #3, a second decomposition additive for hydrogen peroxide, ozone, was utilized.

Example #3

Rendering cooker
Sample size 5 gallons
pH adjusted to 5.5
Sample recirculated at 10 gpm through a Burks regenerative turbine pump throttled by pinch valve assembly to 100 psi. Hydrogen peroxide into suction line at 300 ppm. Ozone as a 6% gas stream generated by a corona discharge type ozonater on dried air was added into the air inlet for the Burks pump (suction side). Ozone dose was 10 ppm as ozone. Total recirculation time was 2 minutes.
Odors were completely neutralized.
After sample sat unaerated and undisturbed for 48 hours, the odors did not reoccur.

Example #4

Mixed proteins rendering, plant trial.
Use of chlorine dioxide in scrubber reduced VOC emissions by 88%
pH reduced to 5.5 with sulfuric acid
300ppm 50% hydrogen peroxide added concurrent with 100ppm 38% ferrous sulfate solution
Total VOCs reduced by 96%

In the above examples, odor reduction was measured using the sense of smell and VOC emission measurements using standard emission detectors. It will be appreciated that various other devices and measurement techniques may also be used which conform to standard practices as may be required for a particular processing industry.

The present invention has been described above primarily with reference to removal of odor and/or noxious components from an atmospheric effluent in which the oxidized odor and/or noxious components are oxidized during contact with an aqueous hydrogen peroxide composition to produce substantially non-odor offensive, environmentally acceptable by-product which is solubilized in or adsorbed onto the aqueous hydrogen peroxide composition to form a liquid effluent. As earlier described, the liquid effluent produced by the present invention also offers advantages to influent to the wastewater treatment process.

Figure 2:
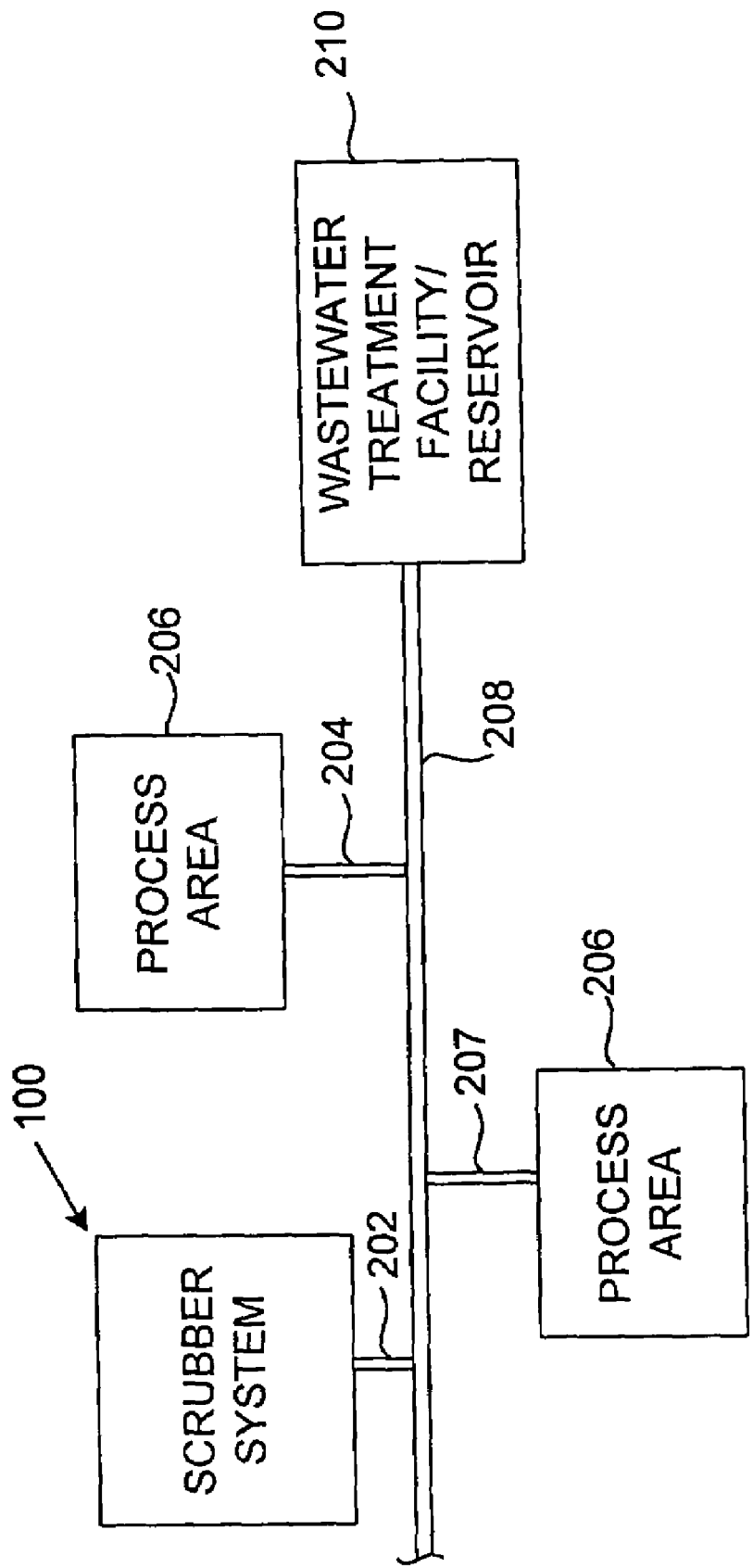
FIG. 2 shows the system of FIG. 1 within a wastewater effluent system of a processing plant illustrating the pretreatment properties of the present invention on the waste treatment facility according to one embodiment of the present invention.

FIG. 2 shows the system of FIG. 1 within a wastewater effluent system of a processing plant illustrating the pre-treatment properties of the present invention on the waste treatment facility according to one embodiment of the present invention. In FIG. 2, liquid effluent is discharged from system 100 earlier described with reference to FIG. 1, for example, through a wastewater pathway 202. As earlier described, the liquid effluent may be discharged by dumping the reservoir or by continual overflow of the liquid effluent from the reservoir. The wastewater pathway 202 may merge with other wastewater pathways 204 exiting from other process areas 206 in the processing plant, for example, wash and rinse waters, chicken feather processing waters, rendering cooker waters, etc. These wastewater pathways 202, 204 eventually converge into one or more wastewater pathways 208 that discharge into one or more large reservoirs in a wastewater treatment facility 210.

When the liquid effluent enters the reservoir at the wastewater treatment facility 210, the liquid effluent is effectively "pre-treated". The liquid effluent contains metal hydroxide complexes, for example, cationic ferric hydroxide complexes, which offer effective colloidal charge neutralization, as well as provide for adsorption of wastewater constituents into its floc matrix. While some of the complexes are utilized by the components of the liquid effluent, a residual amount of these complexes are also available to the other wastewater effluent in the reservoir of the wastewater treatment facility. As wastewater treatment facilities typically purchase additives to accomplish these results, the addition of these charge neutralizing and adsorption species eliminates or greatly reduces any costs incurred by the waste treatment facility.

The present invention has been described above with reference to removal of odor and/or noxious components from an atmospheric effluent in which the oxidized odor and/or noxious components are oxidized during contact with an aqueous hydrogen peroxide composition to produce substantially non-odor offensive, environmentally acceptable by-product which is solubilized in or adsorbed onto the aqueous hydrogen peroxide composition to form a liquid effluent, and to the advantages provided to wastewater treatment processes. The present invention also has application in other areas of processing plants as an effective biocide, especially in areas related to aqueous food transport flumes.

Food primary and secondary processing involves the handling of large amounts of organic materials. As a result of the amount of organics being processed, biological activity is inevitable. In fruit and vegetable processing, large amounts of water are used to wash and transport food through the various processing steps. The transport and wash waters, because of the buildup of organic matter, are very prone to biological growth, as well as accumulation of toxic organic materials such as herbicides and pesticides. A need exists to provide microbial control of these waters without imparting further toxic products to the aqueous food contact streams. Also needed is an economical method for eliminating or reducing the buildup of toxic herbicides and pesticides in the food transport system.

Attempts in the art have been made utilizing oxidizing compounds such as chlorine gas, sodium hypochlorite, hypobromous acid, chlorine dioxide, hydrogen peroxide, peroxy acids, ozone, and permanganate. While some are effective in limiting microbial growth, either toxic by products, cost, or inefficiencies are limiting factors.

The use of chlorine and chlorine dioxide, while effective antimicrobial agents, has come under environmental scrutiny due to the toxic by-products it produces. In contact with amines, toxic chloramines are formed, as well as trihalomethane compounds, which are now prevalent in most ground waters in the United States. Chlorine based technologies also use large quantities of these materials, as they are rapidly consumed by the high organic loading of the aqueous media before they can impart antimicrobial properties. Hypobromous acid produced by the decomposition of sodium bromide by chlorine has been used with some success, but it too is affected by high organic loading and the chlorine substrates, which while reduced, still impart the same toxicities as hypochlorous acid. Hydrogen peroxide has been used with limited success. Hydrogen peroxide is a slow reacting compound with known antimicrobial properties. The reaction rates are too slow for effective, cost advantageous microbial control. Peroxy acids such as peracetic acid have proven to be effective antimicrobial compounds in aqueous systems. Peracids are usually manufactured by the combination of hydrogen peroxide, acetic acid, and inorganic acid catalyst, and various wetting and sequestering agents. Peracetic acid is normally provided in 5 to 15% peracetic acid concentrations. These peracid compounds contain large amounts of the manufacturing precursors, such as hydrogen peroxide, and acetic acid. These peroxy acid materials have a strong pungent odor and residual acetic acids are toxic by ingestion or exposure at 10 ppm in misted form. Peroxy acids are also limited in use by the high costs that are associated with it. Ozone has found limited use in aqueous food transport and processing streams. Ozone is an effective biocide and its high electronegativity is capable of breaking down selected organic compounds. Ozone is associated with extremely high capital investments cost, and the efficiency is limited by poor transfer coefficients from the generated ozone gas phase to the liquid media being treated.

Use of the present invention, in which an aqueous hydrogen peroxide composition of hydrogen peroxide decomposed by ozone is contacted with the transport waters, results in an effective biocide. This allows sterilization of food transport waters with no toxic by-products. Further, in food transport flumes, regulation of the ozone can also break down accumulated pesticide and herbicide compounds from fruit and vegetable washing into simple non-toxic carboxylic acids. This technology offers significant cost and efficiency advantages over current technologies.

EXAMPLE

The following example describes specific aspects of the present invention to illustrate the invention and aid those of skill in the art in understanding and practicing the invention. The example should not be construed as limiting the present invention in any manner.
Pilot plant evaluation of hydrogen peroxide decomposed by ozone in microbiological control.
Volume of evaluative run 100 gallons; Pennsylvania apple wash/transport flume.
BOD=900 ppm
COD=2100 ppm
Significant large organic matter
Recirculated for 36 hours bio count via dip slide=$10^9$
Filtered BOD (0.45 micron)=685 ppm
Filtered COD (0.45 micron)=1725 ppm 300 ppm 50% hydrogen peroxide added, ozone added at 10 ppm into regenerative turbine pump used to recirculate solution. When the addition of hydrogen peroxide and ozone was complete the addition was stopped. The following bio count in colonies was observed:
@ t=4 min bio count=$10^2$
@ t=10 min bio count=none detected
@ t=8 hours bio count=none detected
@ t=12 hours bio count=10
@ t=18 hours bio count=$10^2$
Filtered BOD=210 ppm
Filtered COD=720 ppm As can be seen by this test, microbial control was excellent with good sustained kill of biopopulation. The lowering of the COD showed decomposition of organic material in the sample water. Analysis performed by the customer indicated a sharp drop in toxicity.

Additionally, a non-ionic wetting agent may be added to the aqueous hydrogen peroxide composition to enhance the biocidal activity as earlier discussed with reference to FIG. 1.

Although the foregoing invention has been described in some detail to facilitate understanding, it will be apparent that certain changes and modifications may be practiced within the scope of the appended claims. Accordingly, the described embodiment is to be considered as illustrative and not restrictive, and the invention is not to be limited to the details given herein, but may be modified within the scope and equivalents of the appended claims.

We claim:

1. A system for scrubbing gaseous effluent, the system comprising:
    (a) a packed column comprising (i) a gaseous effluent inlet, (ii) a packing region for housing packing for contacting the gaseous effluent with an aqueous hydrogen peroxide composition, and (iii) a gaseous effluent outlet that directs said gaseous effluent out of said packed column after it has contacted said aqueous hydrogen peroxide composition in said packing region;
    (b) a fluid line in fluid communication with said packed column and arranged with respect to said packed column to remove said aqueous hydrogen peroxide composition from said packed column after it has contacted said gaseous effluent and introduce said aqueous hydrogen peroxide composition into said packing region;
    (c) a source of hydrogen peroxide arranged to provide said hydrogen peroxide to said fluid line; and
    (d) a source of at least one additive arranged to provide said at least one additive directly to said fluid line whereby said at least one additive mixes with said hydrogen peroxide in said fluid line to decompose said hydrogen peroxide to predominantly hydroxyl free radicals and thereby produce said aqueous hydrogen peroxide composition.

2. A system for removing an odorous or noxious component from a gaseous stream, comprising:
    a gas/liquid contactor configured to contact a gaseous stream comprising an odorous or noxious component with a liquid, said gas/liquid contactor comprising a gas inlet, a gas outlet, a liquid inlet and a liquid outlet;

a tank in fluid communication with said gas/liquid contactor and configured to hold said liquid and to receive said liquid from said liquid outlet;

a fluid line configured to pass said liquid from said tank to said liquid inlet;

a first container in fluid communication with said fluid line, wherein said first container comprises hydrogen peroxide; and a second container in direct fluid communication with said fluid line, wherein said second container comprises an additive that catalyzes the decomposition of hydrogen peroxide.

3. The system of claim 2, further comprising a pump connected to said fluid line, wherein said first container is in direct fluid communication with said fluid line at a location upstream of said pump and wherein said second container is in direct fluid communication with said fluid line at a location downstream of said pump.

4. The system of claim 3, wherein said additive comprises an additive that catalyzes the decomposition of hydrogen peroxide to predominantly hydroxyl free radicals.

5. The system of claim 4, wherein said additive comprises an element selected from the group consisting of Groups 3B, 4B, 5B, 6B, 7B, 8B, 1B and 2B of the Periodic Table of Elements and combinations thereof.

6. The system of claim 4, wherein said additive comprises an element selected from the group consisting of the "d" block transition elements and combinations thereof.

7. The system of claim 6, wherein said additive comprises cobalt.

8. The system of claim 3, wherein said additive comprises ferrous sulfate.

9. The system of claim 8, wherein said first container comprises a solution of about 35% to about 50% by weight hydrogen peroxide and wherein said second container comprises a solution of about 20% to about 38% by weight ferrous sulfate.

10. The system of claim 8, wherein said first container comprises a solution of about 50% by weight hydrogen peroxide and wherein said second container comprises a solution of about 38% by weight ferrous sulfate.

11. The system of claim 2, wherein said additive comprises ferrous sulfate.

12. The system of claim 11, wherein said first container comprises a solution of about 35% to about 50% by weight hydrogen peroxide and wherein said second container comprises a solution of about 20% to about 38% by weight ferrous sulfate.

13. The system of claim 11, wherein said first container comprises a solution of about 50% by weight hydrogen peroxide and wherein said second container comprises a solution of about 38% by weight ferrous sulfate.

14. The system of claim 2, further comprising a regenerative turbine pump connected to said fluid line.

15. The system of claim 14, wherein said additive comprises ozone.

16. The system of claim 2, further comprising:

a pH control system; and a third container in fluid communication with said fluid line and comprising a pH control additive.

17. The system of claim 2, further comprising a second additive.

18. The system of claim 17, wherein said second additive catalyzes the decomposition of hydrogen peroxide.

19. The system of claim 17, wherein said second additive comprises a nonionic wetting agent selected from the group consisting of octylphenols, ethylene oxide block copolymers, propylene oxide block copolymers, and combinations thereof.

20. The system of claim 17, wherein said second additive comprises a chelating agent.

21. A system for removing an odorous or noxious component from a gaseous stream, comprising:

a gas/liquid contactor configured to contact a gaseous stream comprising an odorous or noxious component with a liquid, said gas/liquid contactor comprising a gas inlet, a gas outlet, a liquid inlet and a liquid outlet;

a tank in fluid communication with said gas/liquid contactor and configured to hold said liquid and to receive said liquid from said liquid outlet;

a fluid line configured to pass said liquid from said tank to said liquid inlet;

a pump connected to said fluid line;

a first container in direct fluid communication with said fluid line at a location upstream of said pump, wherein said first container comprises hydrogen peroxide;

a second container in direct fluid communication with said fluid line at a location downstream of said pump, wherein said second container comprises an additive that catalyzes the decomposition of hydrogen peroxide to predominantly hydroxyl free radicals;

a pH probe configured to measure the pH of said liquid within said fluid line;

a third container in direct fluid communication with said fluid line, wherein said third container comprises a pH control additive; and a pH controller electrically connected to said pH probe and configured to control the rate of addition of said pH control additive from said third container to said fluid line.

22. The system of claim 21, wherein said additive comprises ferrous sulfate.

23. The system of claim 22, wherein said first container comprises a solution of about 35% to about 50% by weight hydrogen peroxide and wherein said second container comprises a solution of about 20% to about 38% by weight ferrous sulfate.

24. The system of claim 22, wherein said first container comprises a solution of about 50% by weight hydrogen peroxide and wherein said second container comprises a solution of about 38% by weight ferrous sulfate.

25. The system of claim 21, further comprising a second additive.

26. The system of claim 25, wherein said second additive catalyzes the decomposition of hydrogen peroxide.

* * * * *